(12) United States Patent
Nedwell

(10) Patent No.: US 9,933,379 B2
(45) Date of Patent: Apr. 3, 2018

(54) DEVICE FOR DETERMINING THE CHARACTERISTIC IMPEDANCE SPECTRUM OF A TOKEN

(71) Applicant: Jeremy Ross Nedwell, Bishop's Waltham Hampshire (GB)

(72) Inventor: Jeremy Ross Nedwell, Bishop's Waltham Hampshire (GB)

(*) Notice: Subject to any disclaimer, the term of this patent is extended or adjusted under 35 U.S.C. 154(b) by 216 days.

(21) Appl. No.: 14/779,113

(22) PCT Filed: Mar. 21, 2014

(86) PCT No.: PCT/GB2014/050889
§ 371 (c)(1),
(2) Date: Sep. 22, 2015

(87) PCT Pub. No.: WO2014/147413
PCT Pub. Date: Sep. 25, 2014

(65) Prior Publication Data
US 2016/0054246 A1    Feb. 25, 2016

(30) Foreign Application Priority Data

Mar. 22, 2013    (GB) .................................. 1305283.2

(51) Int. Cl.
*G01R 27/28*    (2006.01)
*G01N 27/02*    (2006.01)
(Continued)

(52) U.S. Cl.
CPC ........... *G01N 27/026* (2013.01); *G01N 29/09* (2013.01); *G07D 5/00* (2013.01); *G01N 2291/2698* (2013.01)

(58) Field of Classification Search
CPC ...... G01N 27/02; G01N 27/026; G01N 29/09; G01N 2291/2698; G01N 33/20;
(Continued)

(56) References Cited

U.S. PATENT DOCUMENTS 3,472,063 A    10/1969    Branson
3,663,842 A *    5/1972    Miller ..................... B06B 1/067
                                                    252/62

(Continued)

FOREIGN PATENT DOCUMENTS

DE    103 21 390 A1    12/2004
EP    0 356 582 A1    3/1990
(Continued)

OTHER PUBLICATIONS

Harb, S.M. et al., "Resonator-based touch-sensitive probe", ELSEVIER, Sensors and Actuators A 50 (1995) 23-29, 7 pages.
(Continued)

*Primary Examiner* — Thang Le
(74) *Attorney, Agent, or Firm* — Westman, Champlin & Koehler, P.A.

(57) ABSTRACT

The present invention relates to a device for determining the characteristic impedance spectrum of a token such as a monetary coin, said device comprising: —a point impedance transducer having an inducing element for inducing an ultrasonic movement in the token and a sensing element for detecting the resistance of the token to that induced movement; —a closed system for housing said point impedance transducer; and processing means connected to the point impedance transducer for determining the characteristic impedance spectrum of said token. In particular, the present invention relates to testing whether a token or coin is genuine or a forgery, of sorting coins including from differing monetary systems and/or their denominations, and also providing a "fingerprint" for forged coins.

21 Claims, 3 Drawing Sheets

(51) Int. Cl.
  *G07D 5/00* (2006.01)
  *G01N 29/09* (2006.01)
(58) Field of Classification Search
  CPC .. G07D 5/00; G07D 5/08; G07D 3/06; G07D 3/12; G07D 3/14; G07D 5/02
  USPC ............ 324/76.75, 201–263, 649–727
  See application file for complete search history.

(56) References Cited

U.S. PATENT DOCUMENTS

| | | | |
|---|---|---|---|
| 4,646,571 A | 3/1987 | Kising et al. | |
| 4,854,172 A * | 8/1989 | Lemaster | G01N 29/14 73/32 A |
| 4,971,187 A * | 11/1990 | Furuya | G07D 5/08 194/302 |
| 5,797,475 A * | 8/1998 | Bointon | G07D 5/06 194/317 |
| 5,806,651 A * | 9/1998 | Carmen | G07D 5/08 194/319 |
| 7,400,079 B2 * | 7/2008 | Omura | G01N 29/2456 310/327 |
| 7,685,733 B2 * | 3/2010 | Ohmori | G01B 3/008 33/559 |
| 2007/0210677 A1 * | 9/2007 | Larson | B01L 3/0268 310/338 |
| 2012/0274333 A1 | 11/2012 | Anderson | |
| 2013/0096470 A1 * | 4/2013 | Strunk | A61B 17/22004 601/2 |
| 2015/0300993 A1 * | 10/2015 | Prest | G01N 29/12 148/508 |

FOREIGN PATENT DOCUMENTS

| | | |
|---|---|---|
| EP | 1 667 073 A1 | 6/2006 |
| JP | 09-274675 | 10/1997 |

OTHER PUBLICATIONS

International Search Report and Written Opinion for PCT Application No. PCT/GB2014/050889, dated Jul. 18, 2014, 12 pages.

* cited by examiner

DEVICE FOR DETERMINING THE CHARACTERISTIC IMPEDANCE SPECTRUM OF A TOKEN

CROSS-REFERENCE TO RELATED APPLICATION

This Application is a Section 371 National Stage Application of International Application No. PCT/GB2014/050889, filed 21 Mar. 2014 and published as WO 2014/147413 A1 on 25 Sep. 2014, in English, the contents of which are hereby incorporated by reference in their entirety.

The present invention relates to a device for determining the characteristic impedance spectrum of a token such as a monetary coin. In particular, the present invention relates to testing whether a token or coin is genuine or a forgery, of sorting coins including from differing monetary systems and/or their denominations, and also providing a "fingerprint" for forged coins.

The circulation of fake coins, which are those made by counterfeiters without the approval of the state, is an increasing problem world-wide, and in all countries it is a criminal offence to make or use counterfeited coins. In 2012 it was estimated that 3% of £1 coins in circulation in the UK were counterfeit, and nearly two million counterfeit £1 coins were returned to the UK's Royal Mint in 2010. Whereas it is fairly simple to include anti-forgery features in bank notes, coins are relatively easy to forge and forgeries can be difficult to detect. In addition, the quality of forgeries has significantly increased, making them extremely difficult to detect by simple means. In some cases forgeries have caused the withdrawal of particular coins; for instance, the South African five Rand coin was forged to such a degree that in 2004 the coin had to be redesigned and re-circulated.

Forgeries cause a reduction in the value of genuine money, and can cause inflation due to the increase in the money being circulated in the economy. Generally, there is no reimbursement for counterfeits, a consequence of which is that there is an incentive to pass forged coins on to others, causing them to remain in circulation. In addition, while it may be easy for a trained observer to spot an individual forgery, current automatic detection methods for bulk handling of coins are ineffective at detecting and removing forgeries. Consequently, in many monetary systems the current rate of withdrawal of forged coins from circulation is much less than the rate at which they are introduced, such that the proportion or forgeries in circulation is increasing. Eventually the effects of an increasing level of forgeries may be significant, such as decreased confidence in the currency.

A token or coin is made by fabricating at least one, most often two, dies. The dies carry the reverse image of the coin and provide surfaces for stamping the image onto a coin. Blanks of the metal used to make the coin are annealed and stamped using the die to make a coin, using a force that depends on the material of the coin and its dimensions and design. These are rarely completely copied in a forgery and thus a forged coin that is made from a different material or is slightly different in dimensions may be detected if suitably compared with genuine coins.

For instance, it is well known that forged coins may have a different "sound" from genuine coins, and one well known way of testing a coin is to tap it and listen to the noise that it makes. A forged coin may well sound "tinny". This occurs because of the differences in the way in which the coin is made and the materials it is made from affect the stiffness and mass of the coin. Hence the manufacture of a coin will also affect the way in which the coin vibrates when it is tapped, and thus the sound which is radiated by the coin when it is struck. However, this approach is much more difficult where a coin is a good quality copy and so very similar to a genuine coin. Thus the differences may be very small by comparison with a genuine coin and impossible to detect by means of simply listening.

Attempts have been made to improve this method and, for instance, JP09-274675 proposes a vibrator that strikes a coin, and a microphone which detects the sound the coin makes. The subsequent frequency spectrum is analysed to detect a forgery. However, the differences in a frequency spectrum derived by striking the coin may vary not only as a result of differences in striking the coin, but also as a result of any changes in the surroundings and position of the coin, and so this method may be unreliable.

JP09-274675 uses sound waves which are typically between 20 and 20,000 Hz as a means of detecting a forgery. The vibration is applied in an open system where the small differences that may arise between a forged and genuine coin will be swamped by the large differences due to surroundings, and so the detection is subject to interference leading to false determinations. This prior art refers to detecting and analysing only two or a few frequencies and comparing that detected with the known vibration at those frequencies of known genuine coins. If the determination is above a predetermined threshold, then the coin under test is discriminated accordingly.

A method of characterising coins or tokens which directly measures properties of the coin, which are therefore independent of its surroundings, would enable much better detections to be made.

Thus an aim of the present invention is to provide a significantly improved device for determining a token such as a coin. In particular, an aim of the present invention is for a device to rely directly on measuring a property that may be thought of as the flexibility of a coin as a function of frequency, or more formally its characteristic impedance spectrum.

Hence, the present invention provides a device for determining the characteristic impedance spectrum of a token, said device comprising:
- a point impedance transducer having an inducing element for inducing an ultrasonic movement in the token and a sensing element for detecting the resistance of the token to that induced movement;
- a closed system for housing said point impedance transducer; and
- processing means connected to the point impedance transducer for determining the characteristic impedance spectrum of said token.

One aspect of the present invention is that said ultrasonic vibration comprises a swept sine wave between 50 and 500 kHz over 0.1 seconds.

Another aspect is that said processing means comprises a database for storing known characteristic impedance spectra of known tokens and comparing means for comparing the determined characteristic impedance spectrum of said token with those stored in the database.

Preferably said database stores the characteristic impedance spectra of known forged tokens.

Most preferably, said database stores the characteristic impedance spectra of genuine monetary tokens and their monetary values.

Furthermore said processing means includes means for calculating the monetary value of a plurality of genuine tokens determined by the device.

Preferably said comparing means applies a matching algorithm.

Most preferably said matching algorithm comprises:

$$P_{cu} = \sum_0^n S_u(n) \cdot S_c(n)$$

where $S_c(n)$ is a characteristic impedance spectrum for a known token and $S_u(n)$ is a characteristic impedance spectrum of the token being determined.

Another aspect of the present invention is that there is also a display for displaying the determination of the token.

Preferably the present invention is provided as a hand held device and may further comprise an interface for transferring data.

Another aspect of the present invention is to provide a token sorter comprising an input chute for receiving a token, a token characteristic impedance spectrum determination device disposed adjacent to said input chute, a plurality of output chutes and a diverter, connected to said device and disposed between the input chute and the output chutes for diverting the token according to the determination of the device.

The present invention concerns a means of using a quantity that is related to the flexibility of a coin, that is, the characteristic impedance spectrum of a coin to classify coins and detect forgeries. It provides an accurate way to determine whether a coin is a forgery or not, by determining the characteristic impedance spectrum of the coin and comparing it with that of known good ("genuine") coins.

The present invention is described with reference to the accompanying drawings of which:

Figure 1:
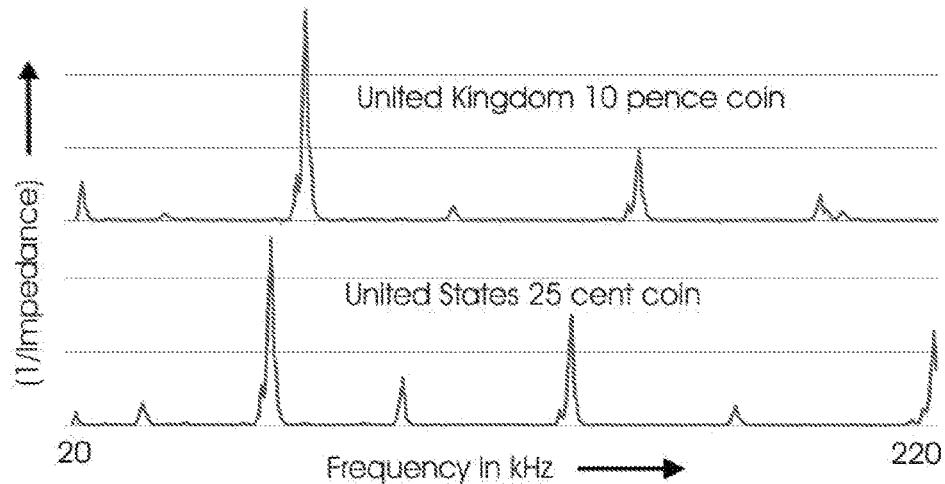
FIG. 1 is a diagram of the reciprocal of the characteristic impedance spectrum of two different coins, a UK 10 pence coin and a USA 25 cent coin, as a function of frequency.

In view of the increasing accuracy of coin forgeries, sound waves are inadequate to determine the veracity of coins. Accordingly, the present invention detects the differences by measuring the characteristic impedance spectrum of the coin by means of a suitable device in contact with the coin. The determination is unaffected by the coin's surroundings.

Generally, the impedance of a coin can be considered to be the complex ratio between a physical driving quantity that causes movement of the coin, such as displacement, to the resistance of the coin to that movement, such as the force that is required to achieve the displacement, as a function of frequency. The characteristic impedance spectrum can be seen as a measure of the impedance or flexibility of the coin at a given point on its surface as a function of frequency.

Thus, if a token or coin is excited by a suitable driving force, such as a sinusoidal signal at a particular frequency or range of frequencies, a coin may display a unique impedance behaviour which changes as a function of the frequency of the driving force. As the frequency of the driving force changes, the ease with which the coin moves under its influence will change, so that the level of movement that is induced may increase and decrease. The change in the impedance of the coin as the frequency changes may include regions and broad swathes of low impedance where the coin bends and flexes more easily than at other frequencies; and broad areas or peaks in which the coin shows a high impedance where it is relatively stiff and resists movement. Depending on the damping of the material the coin is made from, there may be sharp peaks or oscillations in which rapid changes in impedance of the coin occur, or broader peaks in the impedance of the coin where the coin moves easily over a wider frequency range. In some cases these may result because at specific frequencies the coin can vibrate in a number of resonant modes, each of which is a pattern of motion in which all parts of the coin move sinusoidally with the same frequency. Resonances may have a mode shape which describes the direction and amplitude of the movement in parts of the coin, and the fixed phase relationship of each part to the other parts. For any given resonance the coin will have areas in which the displacement is high, the coin flexes easily. The coin will move relatively easily under the influence of a driving force, leading to a sharp fall at that frequency in the resistance to movement and hence in the characteristic impedance spectrum of the coin.

These features of the characteristic impedance spectrum, as revealed by the frequencies and detailed behaviour, are determined by the specifics of the coin. The specifics of the coin include not only the distribution of mass, stiffness and damping within the metallic structure of the coin but also upon the specific metallurgy and engineering of the coin. The present invention determines the characteristic impedance spectrum and therefore can derive whether those particular features are the same for two apparently identical coins.

Needless to say, the characteristic impedance spectrum of coins of different values, or from different currencies, will not be the same, and therefore the characteristic impedance spectrum may be used to determine what coin it is. Indeed, since the materials, weights, dimensions etc. of one coin of one value or currency system will generally be quite different from another, detecting which particular currency and denomination a coin is by comparing it with a database is relatively easy.

As shown in FIG. 1, it is relatively easy to determine the difference between a United States 25 cent coin and United Kingdom 10 pence coin, despite these coins being of similar size. The figure shows typical characteristic impedance spectra for the two coins; in this case, the results are presented as the reciprocal of the characteristic impedance spectrum, as a function of frequency, so that the peaks as the impedance falls are more easily seen. It may be seen that despite the thickness and diameter of the coins being within 2% of each other, the characteristic impedance spectrum varies very significantly from one to another.

Likewise, forged coins have similar but probably much smaller differences in dimensions and material from genuine coins. These differences may include differences in the detailed dimensions of the coin; the alignment and details of the faces, rim and edge decoration; the material or combination of metals from which the coin is forged; the disposition of materials (as for instance with bimetallic coins where a coin is composed of two different materials, often to give a silver coloured centre and a bronze rim); and the force with which the coin blank is struck by the die (since striking the coin may harden the material from which it is made). At least one of these factors will be different in a forgery from that of a genuine coin.

Figure 2:
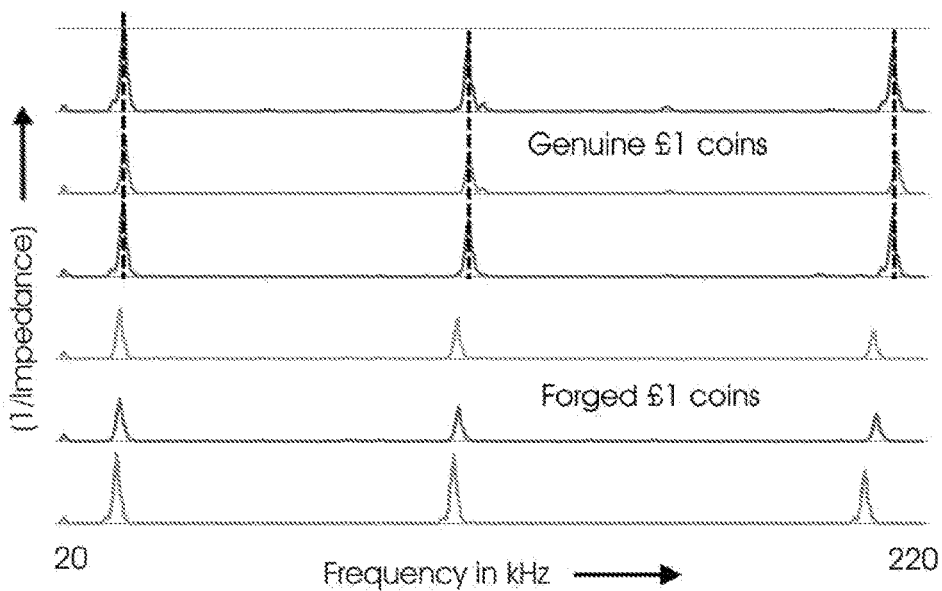
FIG. 2 is a diagram of the reciprocal of the characteristic impedance spectrum of three genuine UK £1 coins and three forged UK £1 coins as a function of frequency.

As shown in FIG. 2, the characteristic impedance spectrum of a forgery is unlikely to be exactly the same as that of a genuine coin. The forgeries were in this case of high quality, and impossible to detect by an untrained eye. The main metallic constituents of the coin were similar for both forgeries and genuine coins, although some very small quantities of rare elements were different in the forgeries. There was no discernible difference in the noise caused by tapping or dropping the coins. FIG. 2 shows typical characteristic impedance spectra for the coins; in this case, the results for the genuine and forged coins are closer than those for different coins as shown in FIG. 1. It may be seen that the characteristic impedance spectra for the three genuine coins are almost identical. However, the three forged coins show smaller and consistent differences from the genuine coins. These are sufficient to determine either visually or by an automatic process that the coins are forgeries. It may be noted that none of these quantities would cause discernible or reproducible differences in a radiated acoustic signature of the coin.

In principle, given the dimensions and material of a known coin, it would be possible to estimate the characteristic impedance spectrum of a genuine coin and compare this with a measured characteristic impedance spectrum of a coin under test to detect whether it was a forgery. However, a simpler approach is to measure the actual characteristic impedance spectrum of one or more genuine coins and compare these with the characteristic impedance spectrum of the coin under test. If its characteristic impedance spectrum is almost identical, the coin under test may be declared genuine. If there is a significant difference, it may be determined to be a fake. Similarly, the characteristic impedance spectrum of the coin under test could be compared with the characteristic impedance spectrum of known forged coins, and if they matched, determined to be a fake.

Clearly, the engineering of genuine coins will change from time to time. However, by keeping a database of the characteristic impedance spectra of examples of various denominations of genuine coins of one or more currency systems, and comparing the characteristic impedance spectrum of a coin under test with the database, it would be possible to detect first the particular currency and denomination; secondly whether if it is a genuine coin or forgery, and thirdly, to "fingerprint" the coin by specifying if genuine the period and mint of manufacture, or if a forgery the particular fraudulent operation from which it originated.

The present invention through the use of measuring the characteristic impedance spectrum of a token or coin may be implemented in a number of embodiments. For example, when sorting coins into those from different currencies and those of different denominations and most especially when done rapidly in bulk automatic sorting. Secondly, the present invention offers a means to detect forgeries, so that they can be withdrawn from circulating currency, or detected and refused at bank tills, shops, and by individuals. Thirdly, because forgeries are generally made by an automatic and continuous process and have small but consistent differences in manufacture, such an apparatus also offers the means to determine a "fingerprint" for a particular forged coin made on a particular illicit machine. This may be of importance to law enforcement agencies, since tracing a particular forged coin back to its source and so may be an important part of detecting forgery operations. Moreover, the ability to uniquely "fingerprint" a forgery may have important applications in legal processes and in particular in prosecuting forgers.

Figure 3:
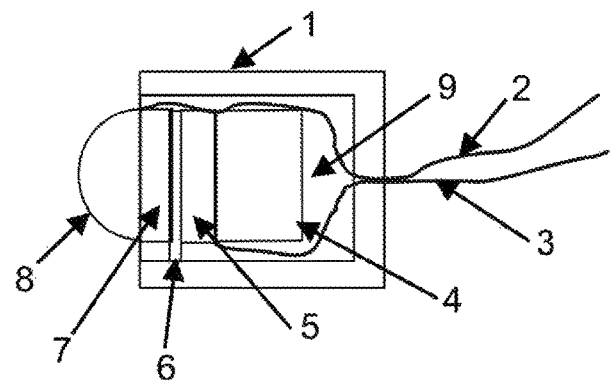
FIG. 3 is a schematic diagram of a transducer employed in the present invention.

The characteristic impedance spectrum of a coin may be determined by means of a suitable point impedance transducer, as shown conceptually in FIG. 3. The characteristic impedance spectrum of a coin is determined by the point impedance transducer which incorporates both a driving element 5 and sensing element 7. The driving element induces movement in the coin, and the sensing element detects the resistance of the coin to the movement induced by the sensing element. The transducer also works equally well if the two elements are interchanged, such that the driving element is adjacent to the coin. In general, the point impedance transducer requires an input, generally a swept sine wave alternating voltage, and will provide as, an output, a signal of the same character, but modulated according to the characteristic impedance spectrum of the coin under test. The input signal and output signal are transmitted via connections 3 and 2 respectively.

Typically, the driving element will be made of a piezoelectric material, or a magnetostrictive material, or other material that changes in shape or volume when a voltage or other driving signal is applied. The driving element will typically be chosen to be a "hard" material such as a piezoelectric, such that it induces a roughly constant displacement in the coin when the electrical signal driving it is constant. If a piezoelectric material is used, a sinusoidal electrical signal of constant voltage may be applied to the driving element to create movement in the coin.

Where the coin is driven at a constant displacement by the driving element, at frequencies where the flexibility is high, that is, the impedance is low, the coin will move relatively easily, and the resistance to movement, typically indicated by the force applied to the sensing element, and hence by the sinusoidal voltage signal it creates, will be low. However, if the coin is driven at frequencies where it is stiff, the force required to displace the coin will be high and the level of sinusoidal voltage created by the sensing transducer will be high. Hence, the combination of the driving and sensing element in the point impedance transducer will measure the characteristic impedance spectrum of the coin.

As shown in FIG. 3 the driving element 5 is typically provided with a backing mass 4 which increases its ability to cause movement in the coin. The driving element is located adjacent to the sensing element. Both elements may be mounted in a canister 1 made of metal or a non-conductive material such as plastic or rubber. Within the canister there is an insulation layer 9 for holding the elements in place and insulating and isolating them from the canister and other structures, and may additionally serve to dampen any vibrations of the transducer which may interfere with the identification of the coin. Both elements are connected to earth via a conductive connection 6. The transducer has an anvil 8, or hard structure, attached to its front face which both prevents wear of the transducer and also is designed to efficiently couple the movement caused by the driving element to the coin, and to efficiently couple the resistance of the coin to movement back into the sensing element.

Figure 4:
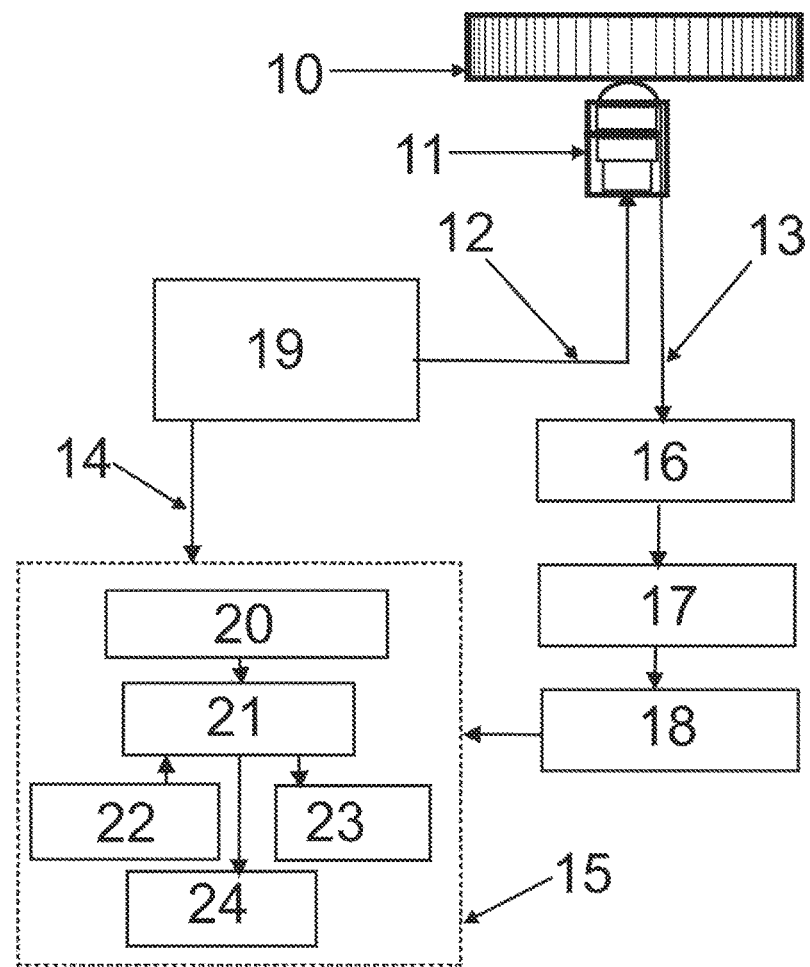
FIG. 4 is a schematic diagram of the device according to the present invention with a coin under test.

With reference to FIG. 4, a carrier (not shown) is used to put the point impedance transducer 11 in touch with the coin 10 since the coin must be in contact with the active face of the point impedance transducer in order that the characteristic impedance spectrum can be measured. Preferably the characteristic impedance spectrum of the coin will be measured at the same point on the coin for both the coin under test and the coins that provide a database for testing the coin against. It should be noted, however, that irrespective of wherever the point impedance transducer touches the coin, the resonant peaks in the characteristic impedance spectrum remain at the same frequency (although their level may increase or decrease), and still could be used to test whether a coin is genuine or a forgery. The best estimates of the characteristic impedance spectrum are generally obtained when the point impedance transducer is pressed to the centre of the flat surfaces of the coin perpendicular to the surface. It may however be easier in some circumstances to allow the coin to roll over the point impedance transducer, such that the contact occurs at the rim of the coin. Provided that the characteristic impedance spectrum of the coin is in this case also measured on the rim for the coins that provide a database for testing the coin against, the database should provide a good basis for testing the coin.

A generator 19 is connected to the point impedance transducer 11 via connection wire 12 to provide the electrical driving signal to the driving element so that it generates vibration in the coin. The output voltage which is generated by the sensing element is typically of low level, and so is conducted by wire 13 and preferably amplified by an amplifier 16 prior to any further processing being undertaken.

In the preferred embodiment, the amplified output is submitted to a root-mean-square (rms) detector 17 and then converted by an analogue to digital (A/D) converter 18. The output of the A/D converter 18 is analysed by a microprocessor assembly 15 which also receives a signal from the generator 19 to obtain details of the input driving signal which has been submitted to the driving element. The microprocessor preferably provides a display 20 of the characteristic impedance spectrum, a database 22 of known characteristic impedance spectra for genuine and forged coins, processing means 21 for processing an algorithm that may be used to match the characteristic impedance spectrum of the coin under test to that database and hence determine whether the coin is genuine or not, an output and warning device 23 for instance incorporating a flashing light that indicates a forgery, and a USB interface 24 that may be used for external devices to communicate with the microprocessor.

Typically, the driving element will cause movement in the coin with a swept sine wave. It is preferred that the wave may be swept from 50 kHz to 500 kHz, and may sweep over this range in say 0.1 seconds.

The output of the sensing element at a given frequency will also be a sinusoidal wave, but of a level that will depend on the flexibility or resistance to movement of the coin at that frequency. Typically where the elements are piezoelectric the output level will indicate a measure of the force that the driving element superimposes on the coin as it moves under its influence. Consequently, if the level of the output of the sensing element is measured as a function of time, and so also of the frequency at which the driving element is driven, an estimate of the characteristic impedance spectrum of the coin can be determined as a function of frequency. Typically, the amplitude of the driving signal to the driving element will be kept constant, so that the impedance of the coin can be estimated as being in proportion to the amplitude of the output from the sensing element. A signal that is indicative of the impedance of the coin at a given frequency can be determined by measuring the amplitude of the voltage generated by the sensing element, for instance, by estimating the root-mean-square (rms) of the sensed signal as a function of time.

The amplified output of the point impedance transducer is passed through the rms detector 17, which measures the changing amplitude of the sensed signal as the frequency changes. The rms detector preferably provides a smoothed amplified signal proportional to the instantaneous level of the received signal, but which has a suitable time constant, allowing the estimate of the level of the signal to change rapidly enough to resolve rapid changes in the impedance of the coin. The time constant will typically have a response time of about 0.1 milliseconds, allowing the characteristic impedance spectrum to be specified as about 1000 frequency points as the driving frequency is changed between 50 kHz and 500 kHz. The characteristic impedance spectrum of the coin, including broad peaks, sharp resonances, and other features will be displayed as a characteristic of this signal.

Alternatively, it is possible to use a single element to both induce movement in the coin and measure the resulting resistance to movement, by allowing one element to provide both functions. For instance, a single element may be driven by a known voltage, to create movement of the coin. The resistance of the coin to this movement would in turn cause a back EMF, or received voltage, in the same transducer element, which may serve to increase or decrease the electrical charge generated by the piezoelectric material. This change in charge may be measured by a variety of means, and hence the flexibility of the coin inferred using a single element. Other means may also be used to measure the characteristic impedance spectrum, for instance the sensing element may be at a separate point on the coin from the driving element, such that the movement of the coin at one point to a known force applied at another could be measured.

It will be appreciated that other physical properties may be used as a measure of the resistance to movement or flexibility of the coin, and as supplied to the driving element and measured by the sensing element. For instance, both the driving element and the sensing element may provide or receive a level of force, displacement, velocity, acceleration or other physical measurements that may be used to infer the resistance to movement of the coin. Whatever measure is used, the ratio between the driving quantity and the resulting sensed measure can serve to estimate a unique quantity corresponding to a measure of the flexibility of the coin. Any resulting relationship between a chosen physical quantity inducing movement in the coin and a chosen physical quantity indicating the detected degree of resistance of the coin to that movement, as a function of frequency, may be used to characterise a coin and its forgeries.

It is preferred to use a driving frequency between 50 kHz and 500 kHz to determine the characteristic impedance spectrum of a token or coin. At frequencies above 500 kHz, the wavelength of the vibration within the material of the coin is comparable with internal random differences caused in the manufacture of the coin. Accordingly, the characteristic impedance spectrum within this frequency range may change as a result of these small random differences and not be related to consistent changes in structure caused by forgery. Hence, these higher frequencies may be ignored when processing the data. Similarly, at frequencies below 50 kHz, the wavelength of the vibration is a large proportion of the size of the coin. Thus, there may be little differences between the characteristic impedance spectrum of a forged coin and a genuine coin at these frequencies.

As noted previously, the frequency of the driving signal is swept between, say 50 kHz and 500 kHz, at a predetermined rate. The frequency may for instance be swept at a linear rate, such that the frequency changes by a fixed number of Hertz per second, or maybe swept at a logarithmic rate, such that the frequency for instance doubles in equal increments of time.

It will be appreciated that there are alternative but equivalent ways of determining the way in which the flexibility of the coin changes as a function of frequency. For instance, one estimate of the characteristic impedance spectrum may be provided by driving the driving element with any arbitrary signal, such as, for instance, white noise, and recording the response of the sensing element. By using a suitable algorithm such as the Fast Fourier Transform (FFT) to estimate the spectrum of the sensed signal, and dividing it by the spectrum of the driving signal, a quantity similar to the characteristic impedance spectrum of the previous example can be obtained.

Where a signal of swept frequency is used, and if the frequency range is well chosen and wide enough, the characteristic impedance spectrum of the coin will contain many changes in level as a function of frequency that depend only on the structure of the coin. These are compared with characteristic impedance spectra measured on coins that are known to be genuine, or with an characteristic impedance spectrum calculated using a suitable model, such as a finite element model. Since the characteristic impedance spectrum of any coin will depend uniquely upon its exact size, the metal it is made from, how hard it is struck etc. it will be possible to determine not only whether the coin is genuine or a forgery, but also to provide a fingerprint that may determine from which press the coin came.

Ideally, there will be provided a large database of characteristic impedance spectra for a wide range of genuine and forged coins. A forged coin may be detected by finding that its characteristic impedance spectrum is different from that of the stored characteristic impedance spectra for known genuine coins, or by finding that its characteristic impedance spectra matches that of a known forgery. In this latter case it will be possible to identify and classify a forgery as coming from a particular source.

Thus, when the characteristic impedance spectrum of the coin has been measured for each coin, it is necessary to recognise whether it indicates the coin is a genuine or forged coin. In the simplest case, a user could be trained to recognise visually the characteristic impedance spectrum of each coin, since as may be seen from FIG. 2 they are often considerably different. However, from FIG. 2, it may also be seen that it might be helpful to have a means to allow the user to overlay examples of the characteristic impedance spectrum of genuine or known forged coins over the unknown coin, in order to help the user identify the coin as genuine or fake by comparison of its characteristic impedance spectrum with the characteristic impedance spectra of the known coins.

To that end, the microprocessor assembly 15, includes a display 20 for displaying the characteristic impedance spectrum of the coin under test, means 21 for matching the impedance to known coins using a database 22 of characteristic impedance spectra and preferably an output 23 giving the best match for the coin under test together with a warning if a forgery.

The input driving and output sensing signals, converted and amplified where required, are submitted to the microprocessor assembly 15, where their level is recorded as a function of time and, since the signal is swept, of frequency.

The matching means 21 may be effected using a suitable algorithm. For instance, a matching algorithm may be performed which compares the characteristic impedance spectrum of the coin under test with the characteristic impedance spectra of known coins. Consider, for instance, where it is desired to estimate the degree to which a characteristic impedance spectrum for a particular coin $S_c(n)$ having n points describing the spectrum as a function of frequency is matched to the equivalent but unknown characteristic impedance spectrum $S_u(n)$. It is convenient and computationally rapid to provide an estimate of the degree of matching by multiplying each frequency point in the characteristic impedance spectrum by the equivalent frequency point in the unknown characteristic spectrum, and integrating the result over all of the points. Thus the degree of matching $P_{cu}$ that the characteristic impedance spectrum matches with the unknown spectrum is given by $$P_{cu} = \sum_0^n S_u(n) \cdot S_c(n)$$

provided that the spectral characteristics are normalised prior to this matching being undertaken. It may be shown that this matching algorithm will provide the highest value where the matching between the known and unknown characteristic is best. This results because where the matching is good, and peaks in the known characteristic impedance spectrum tend to coincide with the peaks in the unknown characteristic spectrum, a high value will be multiplied by a high value, leading to a significant contribution to the sum and a consequent high value. Where the matching is poor, and a peak in one characteristic impedance spectrum coincides with a low value in the other, they will be little contribution to the sum, leading to a low value of the sum. Indeed, the accuracy of the matching algorithm might be improved further where a penalty is paid when peaks exist in one spectrum which do not exist in the other, since this would also tend to indicate that the matching is poor. Thus the best matching reference characteristic impedance spectrum will be the one having the highest value of $P_{CU}$.

Alternatively, it would also be possible to catalogue the frequency at which peaks or other features occur in the characteristic impedance spectrum of the coins in the database, and simply compare these with the equivalent quantity for the unknown coin under test. The best match of these quantities to those of the unknown coin would indicate the best or most likely match.

It will be appreciated that there are other methods by which the characteristic impedance spectrum of a coin may be compared with a database of known coins. For instance, where there is a large database of fake and genuine coins, it would be possible to find say the best ten, or fifty, matches by the preceding means, and then to determine how many of these best matches correspond to fake or genuine coins. Clearly, where the majority or all correspond to real coins the coin under test might be determined to be a real coin, and where the majority or all correspond to fake coins the coin under test might be determined to be a fake coin. However, in the event that the coin under test matched a roughly equal number of each, the result might be deemed ambiguous and other forensic tests applied to the coin to determine its veracity.

Algorithms of this sort are most simply implemented in software on a microprocessor, computer, or similar device. However, it should be noted that it would be equally possible to build analogue electronics that would provide the same function.

Figure 5:
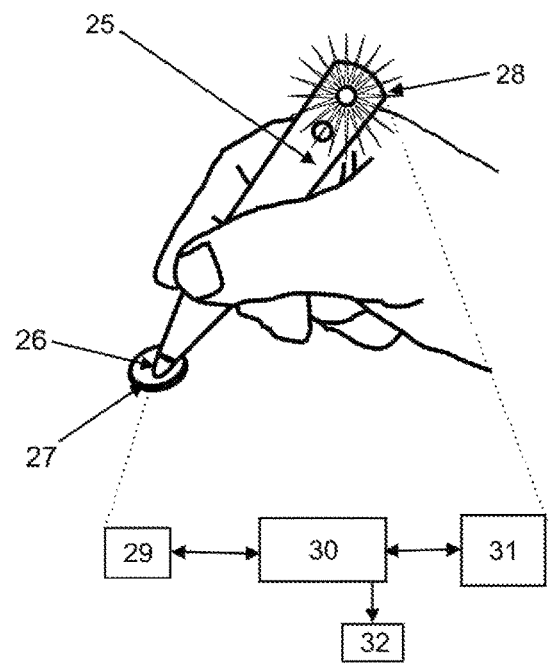
FIG. 5 is a schematic diagram of an embodiment of the present invention in the form of a hand held detector.

As shown in FIG. 5, the present invention extends to a simple hand held forged coin detection pen 25, which is analogous to the forged note detection pens that detect a forged note by chemical or ultraviolet means. The output signal processing means could be disposed also at the tip or in the remainder of the pen. The pen 25 is equipped with the point impedance transducer at its tip 26, which in use is pressed to a coin 27. Similarly to the preceding embodiment, the detection pen is provided with a signal generator, amplifier and rms detector 29, a comparison means 30, a database 31 and an output means 32. The output means 32 may typically illuminate a warning light 28 if a forgery is detected.

The pen may be operated by a switch (not shown) to turn it on. Alternatively, the pen may be activated by the microprocessor monitoring the change in the output signal when the tip is pressed to a coin. By comparing the characteristic impedance spectrum of the coin with its database, the pen could determine whether it is a forgery or genuine. Most simply, the LED warning light 28 would indicate red if the coin was a forgery, allowing forged coins to be refused as tender or green if the coin was genuine. The pen is also provided with a USB interface for allowing the pen to be connected to a computer (not shown), so that the database could be updated as new forgeries or new genuine coins are issued.

An alternative hand held device such as the pen shown in FIG. 5, includes having the point impedance transducer and LED disposed in the pen and the microprocessor disposed separately and the pen and microprocessor connected together by a flexible lead.

Figure 6:
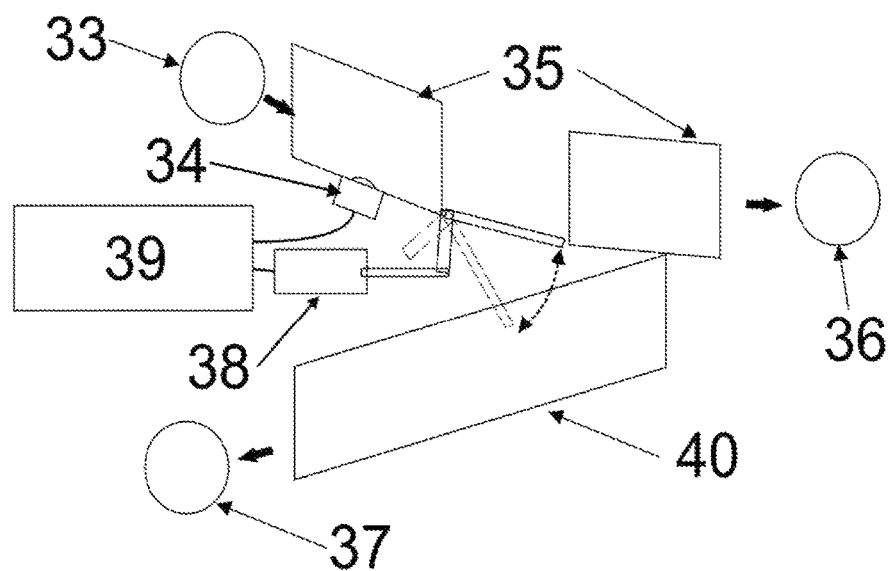
FIG. 6 is a schematic diagram of another embodiment of the present invention in the form of an automatic coin sorter.

As shown in FIG. 6, the present invention also extends to mechanical identification and acceptance of coins, for instance as a point of sale or use of coins and tokens in automatic vending machines. Coins 33 are inserted into a coin chute 35. In rolling down the chute, the coins are brought into contact with the point impedance transducer 34, in this case by rolling over it. During the period the coin is in contact with the transducer, electronics 39 similar to that of the preceding embodiment detects both the denomination of the coin and whether it is genuine. If the coin is forged, unrecognised, or meets another criteria, for instance, that the total value of coins inserted exceeds the value of the goods vended, a solenoid 38 is actuated and the reject coin 37 is rejected down a reject coin chute 40. For the coin 36 that is genuine and suitable for payment, it continues along chute 35 and is accepted. Where one or more coins are inserted, the microprocessor and electronics 39 maintains a record of the value of the genuine coins submitted prior to confirming that the goods or services are released.

It may be appreciated that a variation of this embodiment includes providing multiple solenoids for diversion to a plurality of output chutes which would allow coins to be automatically sorted at high speed into their currency and denomination and forgeries identified and rejected.

The present invention enables particular classes of forgery to be identified or "fingerprinted" by their unique characteristic impedance spectrum, since whereas forged coins from a particular source will have similar characteristic impedance spectra, it is likely that forged coins from a different sources will have dissimilar characteristic impedance spectra. Thus, a forensic tool based on the invention, preferably using a hand-held pen connected by USB or similar to a software processing system on a laptop or similar computer, may be used to characterise particular forgeries, for instance coming from a particular forgery operation or coin press, by means of their unique characteristic impedance spectrum. This would allow government law enforcement authorities or mints to rapidly identify, characterise and trace the source of forgeries for either evidential or intelligence purposes. Characterisation of forged coins may help to identify forger-distributor relationships, the forged coin source, suppliers of materials such as coin blanks and coin presses, distribution networks and routes, and would hence aid in eventual prosecution.

It will be appreciated that the present invention has been described with reference to a number of embodiments and variations and will be appreciated by those skilled in the art that further variations may be envisaged which fall within the scope of the accompanying claims. In addition, it should be appreciated that the drawings are provided as exemplary and similar features whilst being referenced with different reference numerals should be assumed to denote the same feature.

The invention claimed is:

1. A device for determining the characteristic impedance spectrum of a metallic token, said device comprising:
   a point impedance transducer having an inducing element for inducing an ultrasonic movement in the token and a sensing element for detecting the resistance of the token to that induced movement;
   a closed system for housing said point impedance transducer; and
   a microprocessor connected to the point impedance transducer for determining the characteristic impedance spectrum of said token.

2. The device as claimed in claim 1, in which said closed system comprises a canister and insulation disposed between the canister and the inducing and sensing elements.

3. The device as claimed in claim 1, in which said closed system also includes an anvil for coupling the inducing and sensing elements directly to said token.

4. The device as claimed in claim 1, in which said point impedance transducer includes a backing mass coupled to said inducing element.

5. The device as claimed in claim 1, in which said point impedance transducer comprises a single element which both induces the ultrasonic movement and also detects the resistance to that movement.

6. The device as claimed in claim 1, in which said ultrasonic movement comprises a swept sine wave between 50 kHz and 500 kHz over 0.1 seconds.

7. The device as claimed in claim 1, in which said microprocessor comprises a database for storing known characteristic impedance spectra of known tokens and comparing means for comparing the determined characteristic impedance spectra of said token with those stored in the database.

8. The device as claimed in claim 7, in which said database stores the characteristic impedance spectra of known forged tokens.

9. The device as claimed in claim 7, in which said database stores the characteristic impedance spectra of genuine monetary tokens and their monetary values.

10. The device as claimed in claim 7, in which said microprocessor includes means for calculating the monetary value of a plurality of genuine tokens determined by the device.

11. The device as claimed in claim 7, in which said comparing means applies a matching algorithm.

12. The device as claimed in claim 11, in which said matching algorithm comprises:

$$P_{cu} = \sum_{0}^{n} S_u(n) \cdot S_c(n)$$

where $S_c(n)$ is a characteristic impedance spectrum for a known token and $S_u(n)$ is a characteristic impedance spectrum of the token being determined.

13. The device as claimed in claim 1, further comprising a display for displaying the determination of the token.

14. The device as claimed in claim 13, in which said display comprises a two tone or two colour LED.

15. The device as claimed in claim 13, in which said display displays a graph of the characteristic impedance spectrum determined of the token.

16. The device as claimed in claim 1, further comprising an amplifier for amplifying the output from the sensing element.

17. The device as claimed in claim 16, further comprising a root mean square detector processing the amplified output.

18. The device as claimed in claim 17, further comprising an analogue to digital converter for processing the rms amplified output and providing the input to the microprocessor.

19. The device as claimed in claim 18, further comprising an interface for transferring data.

20. A token sorter comprising an input chute for receiving a token, a device as claimed in claim 1 disposed adjacent to said input chute for determining the impedance characteristics of the token, a plurality of output chutes and a diverter, connected to said device and disposed between the input chute and the output chutes for diverting the token according to the determination of the device.

21. The token sorter as claimed in claim 20, in which one of said output chutes is for outputting rejected tokens.

* * * * *